United States Patent [19]

Garcia-Rill et al.

[11] Patent Number: 5,002,053

[45] Date of Patent: Mar. 26, 1991

[54] METHOD OF AND DEVICE FOR INDUCING LOCOMOTION BY ELECTRICAL STIMULATION OF THE SPINAL CORD

[75] Inventors: Edgar Garcia-Rill; Robert D. Skinner; Yuji Atsuta, all of Little Rock, Ark.

[73] Assignee: University of Arkansas, Little Rock, Ark.

[21] Appl. No.: 341,385

[22] Filed: Apr. 21, 1989

[51] Int. Cl.[5] .............................................. A61N 1/00
[52] U.S. Cl. ................................... 128/421; 128/642; 128/784
[58] Field of Search ............... 128/421, 422, 642, 783, 128/784, 785, 423 W, 423

[56] References Cited

U.S. PATENT DOCUMENTS

| | | | |
|---|---|---|---|
| 3,920,025 | 11/1975 | Stasz et al. | 128/423 R |
| 4,141,365 | 2/1979 | Fischell et al. | 128/642 |
| 4,326,534 | 4/1982 | Axelgaard et al. | 128/421 |
| 4,379,462 | 4/1983 | Borkan et al. | 128/786 |
| 4,414,986 | 11/1983 | Dickhudt et al. | 128/786 |

OTHER PUBLICATIONS

Neuromed Multistim Octrode catalog pages (undated but published prior to Apr. 21, 1989).
Neuromed Lamitrode catalog pages (undated but published prior to Apr. 21, 1989).
Neuromed MSCS Multistim catalog pages (1984).
Neuromed Unistim catalog pages (1984).
Neuromed NTS-2000 Neurostimulator Test System catalog pages (undated but published prior to Apr. 21, 1989).
Neuromed Multiprogrammable Spinal Cord Stimulator (MSCS) System catalog pages (undated but published to Apr. 21, 1989).
Neuromed Pain Busters Price List (1986).
PMT Corporation electrode catalog pages (1986).

Primary Examiner—Lee S. Cohen
Assistant Examiner—Scott M. Getzow
Attorney, Agent, or Firm—Browdy and Neimark

[57] ABSTRACT

A method and device for inducing locomotion in animals by electrical stimulation of the spinal cord using long duration pulses (0.2 msec to 2 msec) delivered at low frequencies (0.5 Hz to 20 Hz) epidurally or subdurally to the dorsal columns or dorsal root entry zone at the cervical or lumbar regions of the spinal cord for treating deficits in locomotion.

26 Claims, 7 Drawing Sheets

METHOD OF AND DEVICE FOR INDUCING LOCOMOTION BY ELECTRICAL STIMULATION OF THE SPINAL CORD

BACKGROUND OF THE INVENTION

1. Field of the Invention

The present invention relates to a method and device for inducing locomotion in animals by epidural and subdural stimulation of the cervical and lumbar enlargements of the spinal cord.

2. The Prior Art

Electrical stimulation of the human spinal cord, usually epidurally, has been used for many years to treat chronic pain and abnormal motor control. The bulk of the use of spinal cord stimulation has been directed at pain relief and entails implantation of electrodes along the dorsal (posterior) aspect of the spinal cord along the length of the dorsal (posterior) columns. For certain patients, this has proved successful in alleviating chronic pain. Spinal cord stimulation also has been used in treating multiple sclerosis, spinal cord injury, cerebral palsy, amyotrophic lateral sclerosis, dystonia, torticollis and other neurological disorders. The aim of such stimulation has been to attempt to control or reduce abnormal movements such as spasticity and rigidity. Some success has been reported in using spinal cord stimulation in bladder dysfunction. The use of electrical stimulation of peripheral nerves and spinal cord to promote recovery from trauma and to accelerate nerve regeneration also has been proposed. To the knowledge of the inventors, there are no reports on the successful use of spinal cord stimulation to induce locomotion, that is, of the use of prosthetic spinal cord stimulation to control stepping movements, especially in the case of a completely severed spinal cord.

The usual placement of epidural electrodes is near the affected (painful) dermatome segment. Implantation techniques vary from the use of laminectomy to catheterization via epidural needle. The parameters of stimulation are usually comprised of pulses of short duration, typically 0.05 msec to 0.5 msec, delivered at high frequency, typically 10 Hz to 2000 Hz at voltage amplitudes set by the patient as needed, usually in the range of 1 v to 15 v. Several companies produce various forms of spinal cord stimulators (Avery Labs., Cordis Corp., Medtronic Inc. and Neuromed Corp.). Some of these types of stimulators will be briefly discussed below, particularly with respect to their stimulus capabilities. These differ in the number of electrodes which can be controlled and in the ranges of the stimulus parameters that they are capable of generating. Units may be powered and controlled through radio frequency coupling from an externally powered unit or be totally implantable (see Sherwood, 1988).

The following is a list of patents and journal articles which relate to the electrical stimulators in use for the treatment of pain and movement disorders. Each will be discussed below.

| Patent No. | Inventor | Patent No. | Inventor |
| --- | --- | --- | --- |
| 3,654,933 | Hagfors | 4,539,993 | Stanton |
| 3,724,467 | Avery et al. | 4,558,703 | Mark |
| 3,822,708 | Zilber | 4,598,713 | Hansjurgens et al. |
| 3,920,025 | Stasz et al. | 4,649,935 | Charmillot et al. |
| 4,044,774 | Corbin et al. | 4,686,991 | Dufresne et al. |
| 4,379,462 | Borkan et al. | 4,688,574 | Dufresne et al. |
| 4,459,989 | Borkan | 4,719,499 | Padjen et al. |
| 4,492,233 | Petrofsky et al. | 4,750,499 | Hoffer |
| 4,512,351. | Pohndorf | 4,754,759 | Allocca |
| | | 4,759,368 | Spanton et al. |

Russian Patent No. 596,247
Jobling et al., "Electronic Aspects of Spinal-Cord Stimulation in Multiple Sclerosis", Medical & Biological Engineering & Computing Journal, January 1980, pp. 48–56;
Garcia-Rill, E., "The basal ganglia and the locomotor regions", Brain Res. Rev., 11:47–63, 1986;
Garcia-Rill, E. and R.D. Skinner, "The mesencephalic locomotor region. I. Activation of a medullary projection site", Brain Res., 411:1–12, 1987a;
Garcia-Rill, E. and R.D. Skinner, "The mesencephalic locomotor region. II. Projections to reticulospinal neurons", Brain Res., 411:13–20, 1987b;
Garcia-Rill, E., R.D. Skinner and J.A. Fitzgerald, "Chemical activation of the mesencephalic locomotor region", Brain Res., 330:43–54, 1985;
Sherwood, A.M., "Spinal Cord Stimulation", The Encyclopedia of Medical Devices and Instrumentation, J. Webster, Ed., Wiley & Son, New York, Vol. 4, pp. 2652–2667,1988; "Control of walking and running by means of electrical stimulation of the mid-brain", Biophysics, 11:756–765, 1966; and Skinner, R.D. and E. Garcia-Rill, "The mesencephalic locomotor region (MLR) in the rat", Brain Res., 323:385–389, 1984.

Jobling et al. disclose experiments using spinal-cord stimulation for cases of multiple sclerosis. Electrodes were placed in the mid-line of the posterior epidural space at the mid or upper thoracic level. Stimuli were applied at a frequency of 33 Hz with pulse durations between 0.05 msec and 2.0 msec. The electrical stimulation produced improved bladder sensation and control and, also, motor power and endurance. It should be noted that these patients could walk voluntarily without the need for stimulation and the stimulation was used only to help control untoward movements.

The Russian patent discloses the use of spinal-cord stimulation using pulses of 400 to 450 msec duration with an amplitude of 4–12 volts. This is an example of electrical stimulation being used to promote recovery from trauma, and not for specific motor control.

Borkan discloses a non-invasive multiprogrammable tissue stimulator which can be used to stimulate the cervical area of the spinal cord, the brain, the cerebellum or the individual nerve fibers or bundles thereof to elicit motor, sensory, neurologic, physiologic or psychological responses. According to this patent, the subcutaneously implanted receiver can be non-invasively programmed any time after implantation to stimulate different electrodes or change stimulation parameters such that a desired response can be attained. Although the patent mentions the possibility of using the device to stimulate the cervical area of the spinal cord to elicit motor responses, the patentee does not discuss the signal ranges which are available using his device, nor does he indicate which, if any, signal value will actually induce locomotion. Further, the motor responses referred to incidently by the patentee are merely unconnected movements. The patentee does not indicate that he can elicit locomotion, which is a specific pattern of movements which are, in their full form, stepping movements.

Charmillot et al. disclose the treatment of neurovegetative disorders by applying electrically induced energy to the brain. The specific electromagnetic wave energy disclosed in the patent consists of rectangular d.c. pulses having a pulse duration of 0.5 to 5 msec and a voltage of from 10 to 100 mv with a repetition frequency of from 10 to 100 Hz and a.c. pulses having a frequency of from 20 to 100 MHz modulated with a frequency of modulation of from 2.5 to 6,000 Hz. This method of stimulation of the brain is aimed at treating complex behavioral problems, not the control of movement.

Allocca discloses an apparatus and method for generating a train of up and down and up-staircase shaped electrical pulses whose peak negative amplitude is two-thirds of its peak positive amplitude and whose frequency can be varied between 1 Hz and 1,000 Hz, and applying these electrical pulses to the body for the treatment of nerve function, impairment and pain. No claims of locomotion control are made.

Padjen et al. disclose a stimulator for muscle stimulation or cranial electro-therapy stimulation. While the embodiment described relates to an instrument maintained externally to the patient, the patentee states that "a similar instrument can be internally implanted within the patient to provide direct stimulation on the nerves or spinal-cord." No indication is given as to the various values for the parameters as possible through the use of the device, especially in terms of the control of movement.

Mark discloses a device for treating sea sickness which involves the application of electrical stimulation to the patient's skull. The variable timing generator provides a frequency range that is variable between 1 and 5 pulses per second. The impulse generator is adjustable between 100 and 300 msec, with the current being adjustable between 0.5 and 3.8 mA. Locomotion control is not discussed.

Stasz et al. disclose a body stimulation system which uses implantable electrodes to stimulate internal portions of the body. Preferably, the low frequency range generated by the transmitter is from about 2 kiloherz to approximately 10 kiloherz. The system is used for stimulating the peroneal nerve in paraplegics, but no claims are made as to how such a stimulation is useful in controlling walking movements.

Zilber discloses an electrical spinal cord stimulating device for treatment of pain. The transmitter in this device is designed to transmit a rectangular pulse of approximately 250 msec. in duration with a repetition rate of from 5 to 200 pulses per second. Control of movement with such a device is not discussed.

A number of the patents listed disclose stimulators without disclosing the ranges of the stimulation parameters which are available through the use of the devices. The Spanton et al. and Dufresne et al. patents disclose electrical stimulators for the treatment of pain. Stanton discloses a tissue stimulator for stimulating muscles using electrodes implanted along the sides of the spine. Hansjurgens et al. disclose a device for electro-stimulation therapy.

Petrofsky and Hoffer disclose the use of electrical stimulation systems for "restoring" motor function of paralyzed muscles. The idea behind these stimulators is to induce locomotor-like movements by stimulating different muscles to contract at different times to produce walking movements. This requires that a program of the sequence of muscle contractions be intrinsic to the device. While this method could produce a rough form of walking, muscles or parts of muscles deep below the skin are difficult to activate and stepping can appear fragmented. In addition, very high currents are required to cause muscular contraction, and the effects of such currents on the underlying skin, muscle and nerve tissue are yet to be determined.

A variety of electrodes are known which can be implanted for applying electrical stimulation to the spinal cord as discussed above for the treatment of pain. Several of these electrodes are shown by Borkan et al., Avery et al., Corbin et al., and Hagfors.

Pohndorf discloses an introducer for a neurostimulator lead which is to be inserted into the epidural space of the spinal cord.

None of these stimulators disclose a device by which electrical pulses having a relatively long duration between 0.2 msec and 2 msec and a low frequency between 0.5 Hz and 20 Hz can be applied directly to the spinal cord in order to induce locomotion.

Over 20 years ago, experiments in the decerebrate cat revealed that stimulation of an area in the posterior midbrain induced normal-type locomotion on a treadmill (Shik et al., 1966). This area was termed the Mesencephalic Locomotor Region (MLR). During the past eight years, the first-named inventor has been working on the anatomical connections of the MLR (for review, see Garcia-Rill, 1986), demonstrating its presence in the rodent brain (Skinner and Garcia-Rill, 1984), and discovering that localized injections of neurotransmitters injected into the MLR could be used to induce locomotion (Garcia-Rill et al., 1985). Recently, the main descending projection target of the MLR, the medioventral medulla (MED), was reported to induce locomotion following electrical and chemical activation (Garcia-Rill and Skinner, 1987a, 1987b). The studies in the laboratory of the present inventors, then, have progressed from the midbrain to the medulla, and now, by the present invention, to the spinal cord.

The methods previously used to improve locomotion by electrically stimulating the muscles, either with implanted electrodes or with external electrodes, have significant disadvantages in their practical application. In particular, as briefly discussed above, very high currents are required in order for movement to occur. These large currents may cause irreparable damage to the nerve and/or muscle tissue in the former case and to the skin in the latter. Further, in order to take a step, a large number of muscles are involved which must be stimulated in a particular sequence. It is very difficult, in fact, nearly impossible to duplicate the normal sequence by merely stimulating the muscles. Additionally, if not all the muscles involved in the walking process are stimulated, the method will not be effective in producing normal-type walking. Since there are a large number of muscles involved, it is nearly impossible to stimulate them all in the proper sequence.

Previous investigations, using brainstem stimulation to induce walking, revealed that very low current levels applied to localized areas of the brainstem can produce normaltype walking. That is, the full range of muscular contractions were elicited in the required pattern for a single step by electrically stimulating the brainstem. This locomotor pattern for producing locomotion is generated at the level of the spinal cord. That is, the full program of muscular contractions is found in spinal pattern generators which are located in the cervical and lumbar enlargements of the spinal cord. Brainstem stimulation merely triggers this preprogrammed pattern of contractions.

The methods involving direct stimulation to the midbrain or the medulla, however, have significant problems in clinical application. Even if it were possible to have a living person implanted with electrodes in their brain, the location of the MLR and MED in relation to respiratory and cardiovascular control centers makes such implants undesirable. In cases of paralysis by damage to the spinal cord, downstream from the midbrain or medulla where the stimulation is applied, the necessary triggering signal does not reach the spinal cord and muscles. Therefore, these techniques will not be effective to actually stimulate locomotion following complete transection of the spinal cord. The use of electrical stimulation of the spinal cord to induce walking as disclosed in the present application represents an effective way of directly activating the intrinsic spinal pattern generators for locomotion, with concomitant manifestation of the normal muscular contractions used in stepping.

As is clear from a study of the above-listed patents relating to electrical stimulators, the low frequencies and long duration pulses required to induce locomotion by direct spinal cord stimulation are outside, or at the edge of, the effective range of the parameters available from the devices conventionally known for the treatment of pain and movement disorders.

SUMMARY OF THE INVENTION

It is an object of the present invention to provide a method and device which can induce locomotion and overcome the disadvantages of the prior art.

It is a further object of the present invention to provide a method and device for inducing locomotion in animals by epidural and subdural electrical stimulation of the spinal cord.

It is a further object of the present invention to provide a method and device for inducing locomotion in animals by epidural and subdural electrical stimulation using specific pulse durations and pulse frequencies.

Accordingly, the present invention provides a method for inducing locomotion in animals using an optimal pulse duration of 1 msec. Effective pulse durations of 0.2 msec to 2 msec have been observed. The optimal pulse frequency was found to be 2.5 Hz; effective pulse frequencies of 0.5 Hz to 20 Hz have been observed.

According to the present invention, the best sites for electrode placement have been at the level of the cervical and/or lumbar enlargements and one or two segments anterior to the enlargements (pre-enlargement sites). In order to induce hindlimb (or leg) locomotion, the lumbar enlargement and pre-enlargement can be stimulated at frequencies of 0.5 Hz to 10 Hz. In order to induce hindlimb (or leg) locomotion by stimulation of the cervical enlargement and pre-enlargement, frequencies must be in the range of 3 Hz to 20 Hz. It should be noted that, to best induce alternation of the forelimbs (or arms), the cervical enlargement must be stimulated at lower frequencies, i.e., 0.5–2.5 Hz. Electrodes may be placed epidurally or subdurally directly on the surface of the spinal cord, along the dorsal or posterior columns, or along the dorsal root entry zone bilaterally, with equivalent effects.

Still other objects, features and attendant advantages of the present invention will become apparent to those skilled in the art from a reading of the following detailed description of embodiments constructed in accordance therewith, taken in conjunction with the accompanying drawings.

BRIEF DESCRIPTION OF THE DRAWINGS

The invention of the present application will now be described in more detail with reference to the preferred embodiments of the device, given only by way of example, and with reference to the accompanying drawings, in which.

DETAILED DESCRIPTION OF THE PREFERRED EMBODIMENT

Figure 1:
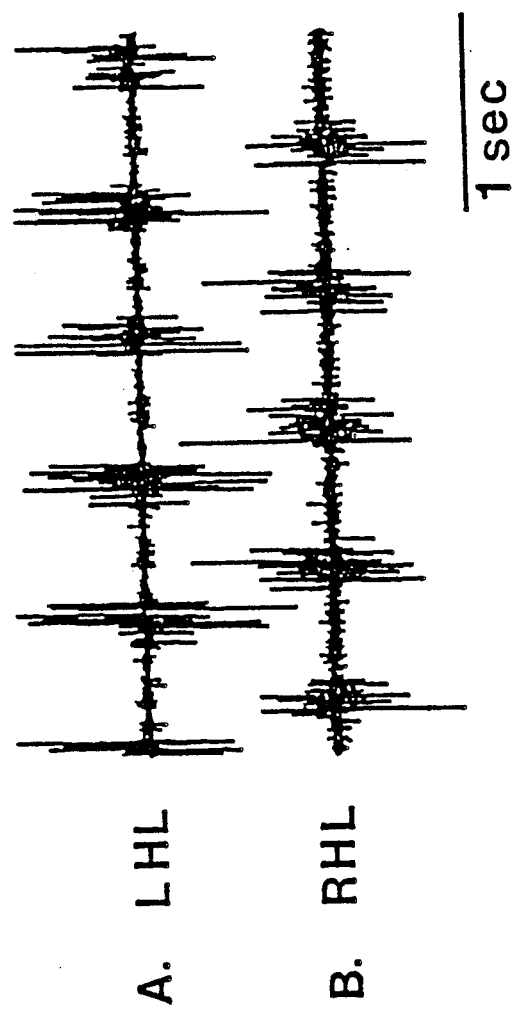
FIGS. 1A and 1B show hindlimb muscle alternation (EMGs during actual locomotion) induced following activation of the cervical enlargement according to the present invention.

The present invention relates to a method and a device for inducing locomotion in animals by electrical stimulation of the lumbar enlargement and the cervical enlargement areas of the spinal cord. It is also possible to induce locomotion by stimulation of the one or two segments anterior to the lumbar and/or cervical enlargements, i.e., the lumbar and cervical pre-enlargements. These sites provided the best results in the experiments, as will be discussed below.

As described above, the spinal cord generates locomotor patterns which produce walking or locomotion. In the prior art, electrically stimulating the brainstem elicited the full range of muscular contractions for a single step. According to the present invention, this locomotor pattern is being triggered locally, directly on the spinal cord in order to read off the programmed pattern.

In the prior art methods of stimulating the MLR and MED, particular stimulus parameters were necessary to elicit locomotion. Likewise, according to the present invention, the cervical enlargement or pre-enlargement and lumbar enlargement or pre-enlargement areas of the spinal cord also require specific stimulus configurations. Stimulation of the MLR requires pulses of 0.5–1 msec duration delivered at 20–60 Hz, while the MED is sensitive to slower frequencies (5–40 Hz). The present studies, as will be explained in more detail below, discovered that stimulation of the cervical enlargement or pre-enlargement of the spinal cord required pulses of 0.2–2 msec duration delivered at 3–20 Hz to induce hindlimb locomotion, while stimulation of the lumbar enlargement or pre-enlargement required similar duration pulses delivered at 0.5–10 Hz, with optimal frequencies around 2.5 Hz. The electrodes may be placed epidurally or directly on the surface of the spinal cord, along the dorsal or posterior columns, or along the dorsal root entry zone bilaterally, with equivalent effects.

Experiments were carried out in adult cats and later confirmed in rats. The animals were anesthetized with halothane, and a precollicular transection performed using suction ablation. Laminectomies in the cervical enlargement and the lumbar enlargement were made to allow placement of stimulating electrodes epidurally and subdurally. In some cases, a transection was made at the $T_6$ level of the spinal cord and only the area of the lumbar enlargement was stimulated electrically.

Two different preparations were used, actual and fictive locomotion. In the former, animals were suspended over a moving treadmill, electromyographs (EMG) of hindlimb muscles were recorded using double hooked wire electrodes and electrically-induced locomotion was assessed by EMG activity. In the other preparation, animals were artificially ventilated and paralyzed with flaxedil (8 mg/Kg/hr), neurograms (NG) of hindlimb nerves were recorded and electrically induced fictive locomotion was assessed by NG activity. The actual locomotion preparation allows study of real-time walking while the fictive locomotion (paralyzed) preparation eliminates sensory feedback and allows study of purely "motor" activity. Several types of stimulating electrodes were used, including 100 $\mu$ wire, 300 $\mu$ wire, disk electrodes, coils, etc. The most effective electrodes were 5–10 sq mm in area.

Our results show that stimulation of the cervical enlargement epidurally or subdurally induced actual and fictive locomotion, provided that long duration, low frequency stimuli were used. Stimulation could be carried out in the pre-enlargement segment $C_4$ as well as within the cervical enlargement ($C_5-T_1$). Stimulation on the surface of the cord (subdurally) was found to be effective when applied to the dorsal columns as well as to the dorsal root entry zone.

FIGS. 1A and 1B show hindlimb muscle alternation (actual locomotion) induced following activation of the cervical enlargement using 0.5 msec pulses delivered at 10 Hz to the epidural space overlying spinal cord segment $C_7$. FIG. 1A shows contractions of the left hindlimb (LHL) gastrocnemius muscle and FIG. 1B show contractions of the right hindlimb (RHL) gastrocnemius muscle induced during stimulation of the cervical enlargement (time calibration bar—1 sec.).

Stimulation of the lumbar enlargement epidurally or subdurally induced actual and fictive locomotion as long as long duration, low frequency stimuli were used. Stimulation could be carried out in the pre-enlargement segments $L_1-L_2$ as well as within the lumbar enlargement ($L_3-S_1$). Stimulation on the surface of the cord (subdurally) was found to be effective when applied to the dorsal columns as well as to the dorsal root entry zones.

Figure 2:
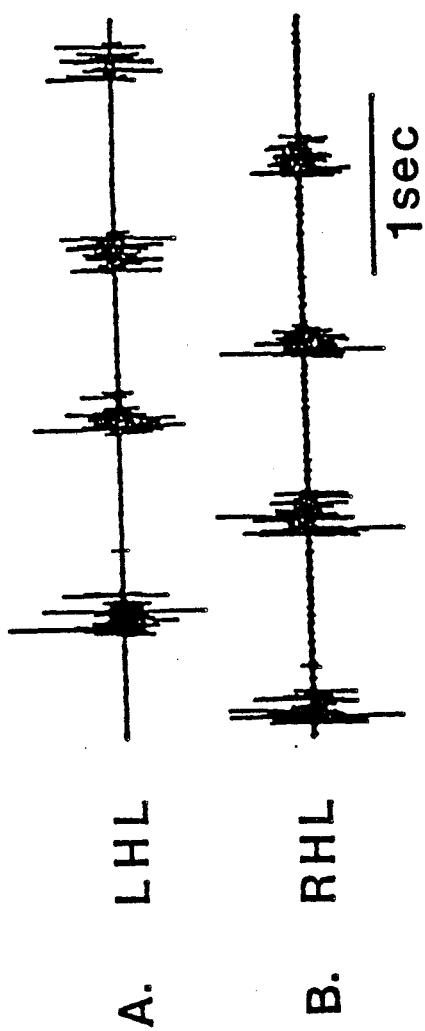
FIGS. 2A and 2B show hindlimb muscle alternation (actual locomotion) induced following activation of the lumbar enlargement according to the present invention.

FIGS. 2A and 2B show hindlimb muscle alternation (actual locomotion) induced following activation of the lumbar enlargement using 0.5 msec pulses delivered at 2.5 Hz to the epidural space overlying spinal cord segment $L_6$. The two records shown are of the same muscles as in FIGS. 1A and 1B, except that locomotion was induced following stimulation of the lumbar enlargement (time calibration bar—1 sec.).

Figure 3:
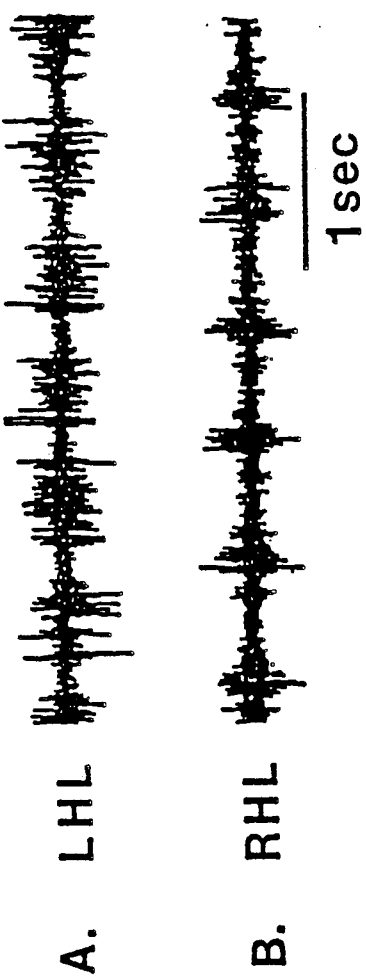
FIGS. 3A and 3B show hindlimb nerve alternation (neurograms during fictive locomotion) induced following activation of the lumbar enlargement according to the present invention.

FIGS. 3A and 3B show hindlimb nerve alternation (fictive locomotion) induced following activation of the lumbar enlargement using 0.5 msec pulses delivered at 3 Hz to the epidural space overlying spinal cord segment $L_6$. The two records show neurogram recordings from left hindlimb (LHL) and right hindlimb (RHL) branches of the tibial nerve going into the gastrocnemius muscle (time calibration bar—1 sec.). Note the different signal-to-noise ratios in the neurograms in FIGS. 3A and 3B, as compared with that of the EMGs in FIGS. 1A, 1B, 2A and 2B.

Figure 4:
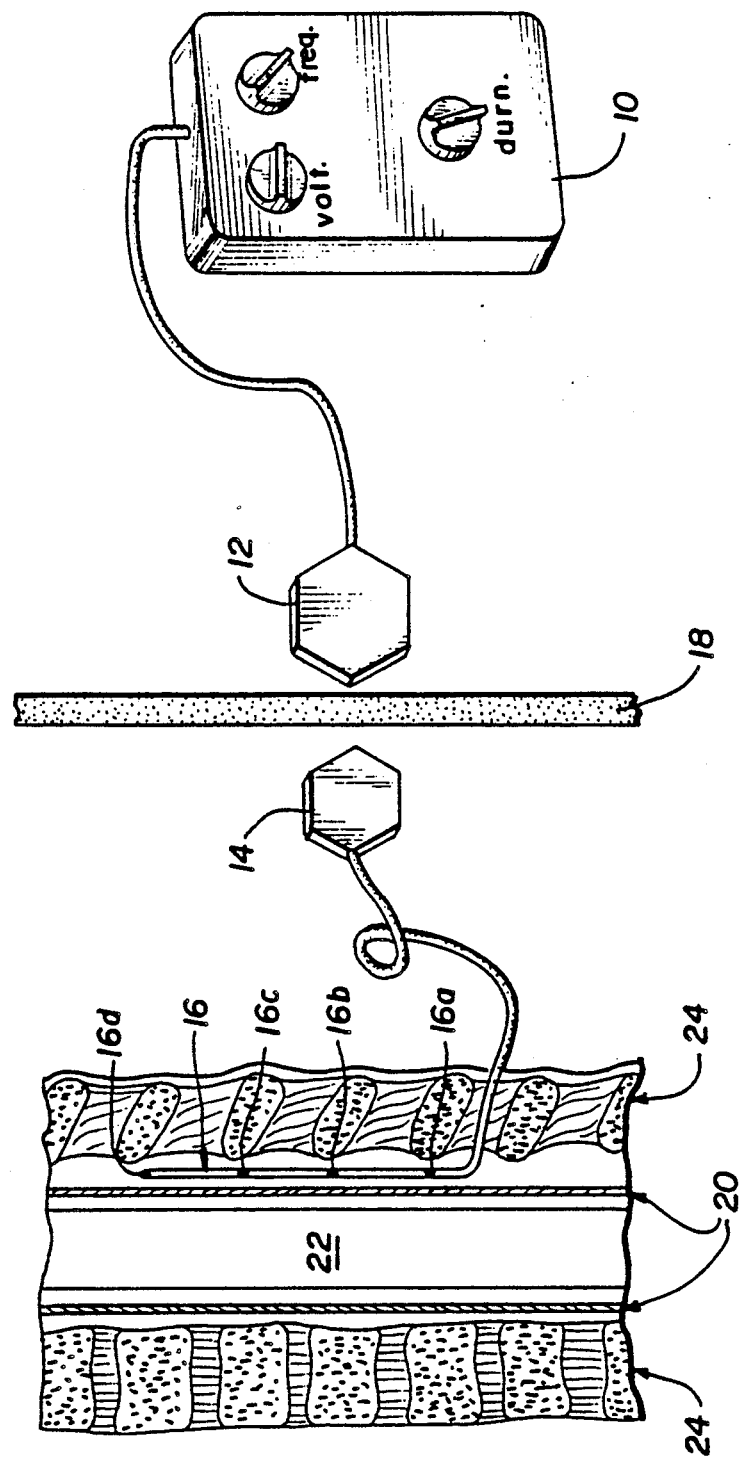
FIG. 4 shows the device for inducing locomotion according to the present invention with an electrode placed between the vertebrae and the dura mater.
Figure 5:
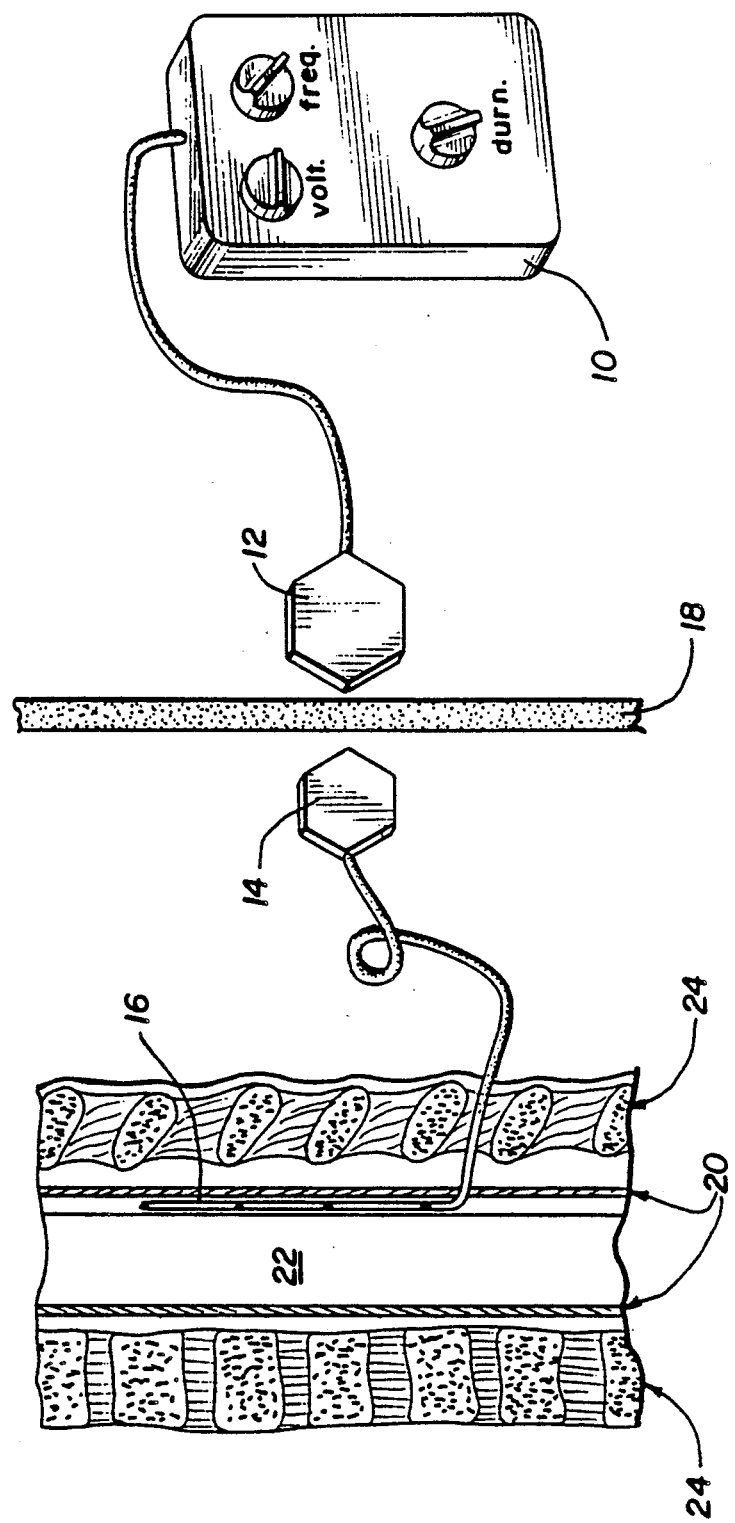
FIG. 5 shows the device for inducing locomotion according to the present invention with an electrode placed between the dura mater and the spinal cord.
Figure 6:
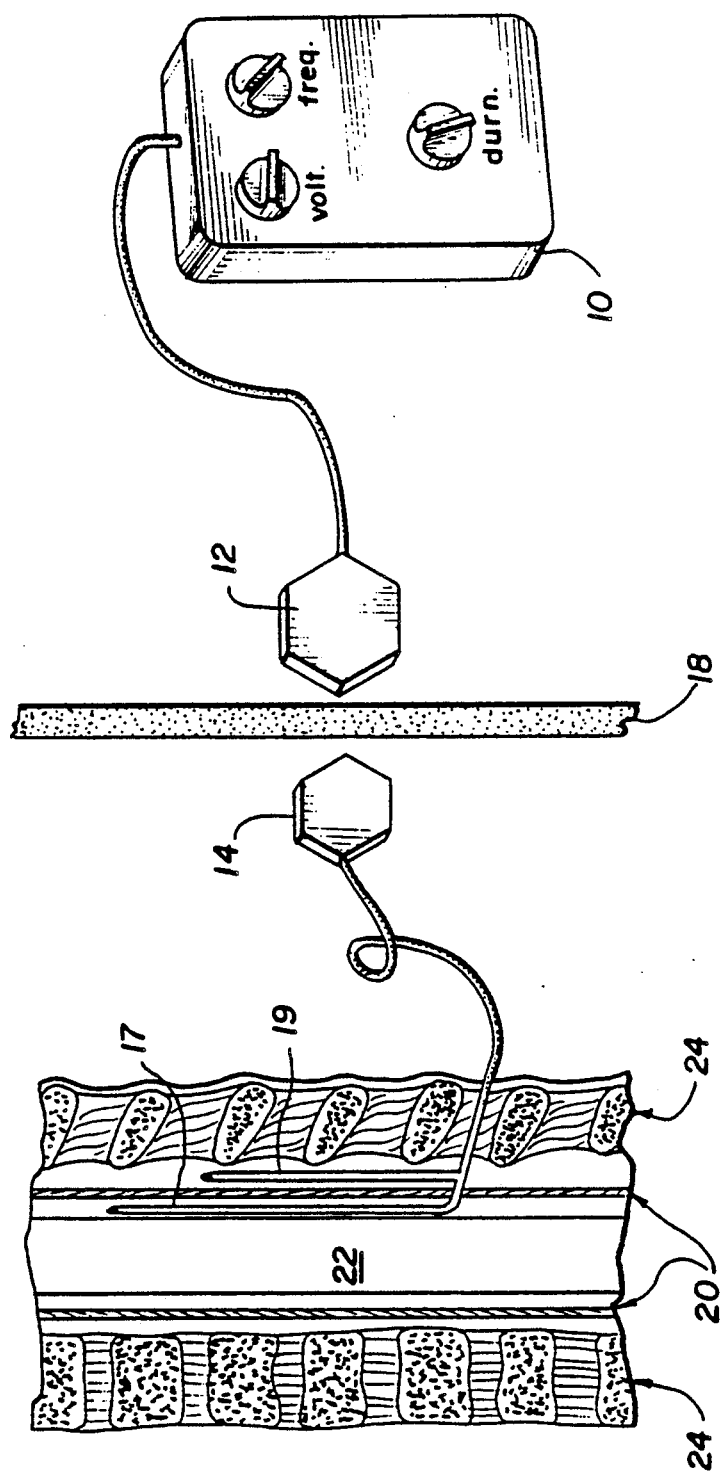
FIG. 6 shows the device for inducing locomotion according to the present invention with a cathode placed on the spinal cord and a reference electrode on the vertebrae.

FIGS. 4-6 schematically show a device for implementing the spinal cord stimulation according to the present invention. The device is shown as it might be used in a clinical setting, consisting of a battery powered radio frequency transmitter control box 10. The patient can dial the voltage (1–15 v), duration (0.2–2 msec) and frequency (0.5–20 Hz) independently using the dials on the control box 10. At the same time, the patient would apply the portable radio frequency transmitter 12 on the skin 18 overlying the implanted radio frequency receiver 14. The receiver 14 is connected to an implanted multipolar electrode 16. The transmitter can also be used to select electrode pairs which will be stimulated, if a multipolar electrode is used. A multipolar electrode with active electrodes 16a, 16b, 16c, and 16d at 1 cm intervals is standard in spinal cord stimulation for the treatment of chronic pain and can be used as the multipolar electrode in the method and device according to the present invention. It is of course possible that any of the standard electrodes available on the market today could be used in the method of the present invention.

Stimulation may be delivered bipolarly between any two electrode sites preferably with the cathode rostrally, or monopolarly by stimulating between a cathode 17 on the spinal cord and a reference electrode 19 clipped or otherwise attached to the vertebrae as shown in FIG. 6. The former method is preferable in clinical application. The electrode should be implanted or placed longitudinally along the dorsal midline overlying the dorsal columns, either epidurally (epidural space 26), as shown in FIG. 4 between the vertebrae 24 and the dura mater 20, or subdurally as shown in FIG. 5. The active electrode sites are oriented to span the pre-enlargement and enlargement segments 22 of the spinal cord. The control box generates the electrical pulses at the required frequency and duration, which are passed to the electrodes through the transmitter and the receiver. In particular, the transmitter 12 receives the RF signal generated by the control box 10 in accordance with the selected parameters. The RF signal is then passed to the receiver 14 which converts the RF signal into electrical pulses which are passed to the electrode 16.

Figure 7:
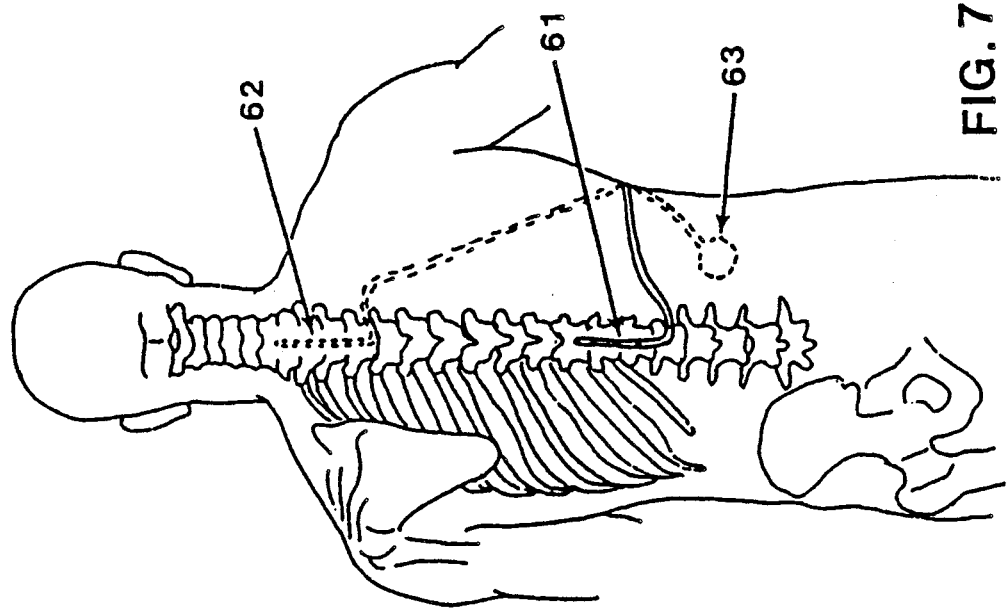
FIG. 7 shows a rear view of the spine in a human illustrating the locations of multipolar electrode implants epidurally or subdurally according to the present invention.

FIG. 7 is a rear view of a human spine showing the locations of the multipolar electrode implant, either epidurally or subdurally, at the level of the lumbar enlargement, shown in solid lines 61, or at the level of the cervical enlargement, shown in slashed lines 62. A receiver is also shown in dashed lines 63 which is led around to the front from either of the placements 61 or 62, and sutured in place subcutaneously in the abdomen for easy access by the transmitter 12.

In accordance with standard practice concerning the use of electrical stimulation for the treatment of pain, in clinical practice the patient could control the electrode pairs between which stimulation would occur on a trial and error basis. In other words, for each patient, in order to effect the inducement of locomotion, different electrode pairs may need to be stimulated. The patient and/or his physician, would determine which electrode pair works best for him. It is understood that a researcher using the method and device according to the present invention would determine which pairs work best for the animal with which he is working.

Specific ranges of 0.2–2 msec for the pulse duration and 0.5–10 Hz for the frequency to induce locomotion by stimulating the lumbar region and 0.2–2 msec at 3–20 Hz to induce locomotion by stimulating the cervical region are preferable. However, it is also possible that using durations and frequencies above and below those ranges may also induce locomotion.

In order to accomplish induced locomotion according to the present invention, it is not necessary that the electrodes be of any particular shape, because disks, coils, bare wires, etc. have been used to induce locomotion when activated appropriately. Electrode dimensions in the range of 5 sq mm to 10 sq mm in area have been found to require the lowest voltages. For long-term implantation, noble metals should be used and the rostral electrode should be the cathode, in keeping with current clinical practice. The best sites for electrode placement have been at the level of the cervical and/or lumbar enlargements and one or two segments anterior to the enlargements (pre-enlargement sites). Known electrodes used for the treatment of pain may be used in laboratory or clinical settings.

It is understood that the design of the precise circuitry used in the control box, transmitter and receiver is well within the skill of one ordinarily skilled in the art.

The usefulness of the invention is in its clinical application. In cases of spinal cord injury/stroke in which total control of locomotion is lost, there is a considerable loss of muscle mass, or atrophy, of the muscles innervated by the spinal cord below the level of the lesion. This atrophy usually occurs almost immediately after the trauma which caused the loss of control. However, after such a trauma it is not possible to begin physical therapy immediately to prevent atrophy of the muscles.

Implantation and use of the device according to the present invention may help maintain muscle mass by "exercising" the muscles when the spinal cord is stimulated. In particular, the spinal cord would be stimulated causing the legs and arms of the patient to move. Such stimulation could be carried out in the standing, sitting, or lying position. This movement would exercise the muscles of the limbs so as to prevent, or at least lessen, the atrophy of the muscles.

In spinal cord injury/stroke cases in which the patient is able to stand but not walk, stimulation of the spinal cord may be used to induce walking. Such patients usually stand with the aid of a wheeled "walker" and the movement of the limbs induced by spinal cord stimulation would provide the necessary propulsion. In spinal cord injury/stroke cases in which the patient is able to be held upright by a wheeled walker (whether or not the patient has the ability to support the body), the movement of the limbs induced by spinal cord stimulation would provide the necessary propulsion to move about.

The application of this invention is not limited to spinal cord injury or stroke victims but may be used in any disorder in which locomotion and/or rhythmic limb movement is desired.

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

What is claimed is:

1. A method of inducing locomotion in animals comprising electrically stimulating the spinal cord using pulses having a duration between 0.2 msec and 2 msec delivered at frequencies between 0.5 Hz and 20 Hz wherein said stimulation is at a locus on the spinal cord at which such stimulation induces locomotor activity.

2. The method of claim 1, further comprising, prior to said stimulating step, the step of placing electrodes for electrically stimulating the spinal cord epidurally, between the vertebrae and the dura mater.

3. The method of claim 1, further comprising, prior to said stimulating step, the step of placing electrodes for electrically stimulating the spinal cord subdurally, between the dura mater and the spinal cord.

4. The method of claim 1, further comprising, prior to said stimulating step, the step of placing electrodes at pre-enlargement and enlargement segments of the spinal cord to induce locomotion.

5. The method of claim 4, wherein, in said placing step, the electrodes are disposed epidurally, between the vertebrae and the dura mater.

6. The method of claim 4, wherein, in said placing step, the electrodes are disposed subdurally, between the dura mater and the spinal cord.

7. The method of claim 4, wherein the pulses have a duration of about 0.5 msec.

8. The method of claim 4, wherein the pulses are delivered at a frequency of about 2.5 Hz.

9. The method of claim 1, further comprising, prior to said stimulating step, the step of placing electrodes for electrically stimulating the spinal cord at the lumbar pre-enlargement or enlargement segments of the spinal cord and wherein said stimulating step comprises the step of electrically stimulating the spinal cord with pulses having a frequency between 0.5 and 10 Hz to induce hindlimb or leg locomotor activity.

10. The method of claim 1, further comprising, prior to said stimulating step, the step of placing electrodes for electrically stimulating the spinal cord at the cervical pre-enlargement or enlargement segments of the spinal cord and wherein said stimulating step comprises the step of electrically stimulating the spinal cord with pulses having a frequency between 3 and 20 Hz to induce hindlimb or leg locomotor activity.

11. The method of claim 1, further comprising, prior to said stimulating step, the step of placing electrodes for electrically stimulating the spinal cord at the cervical pre-enlargement or enlargement segments of the spinal cord and wherein said stimulating step comprises the step of electrically stimulating the spinal cord with pulses having a frequency between 0.5 and 2.5 Hz to induce forelimb or arm locomotor activity.

12. The method of claim 1, further comprising, prior to said stimulating step, the step of placing electrodes along dorsal column or dorsal root entry zones to induce locomotion.

13. The method of claim 1, wherein the pulses have a duration of about 0.5 msec.

14. The method of claim 1, wherein the pulses are delivered at a frequency of about 2.5 Hz.

15. A device for generating electrical pulses for inducing locomotion, comprising:

control means for controlling the generation of electrical signals having a pulse width between about 0.2 msec and about 2 msec and delivered at a frequency between about 0.5 Hz and about 10 Hz for inducing locomotion by direct spinal cord stimulation; and electrode means shaped and dimensioned so as to permit subdural or epidural implantation and connected to said control means, for receiving the signals and applying the signals to the spinal cord, when in use, at a locus at which such stimulation induces locomotor activity.

16. The device according to claim 15, wherein said electrode means comprises a multipolar electrode having a plurality of electrodes.

17. The device according to claim 15, wherein said electrode means comprises at least one electrode for placement longitudinally on the spinal cord and a reference electrode for placement on the vertebra.

18. A device in accordance with claim 15, wherein said control means is for controlling the generation of electrical signals having a pulse width between about 0.2 msec and about 2 msec and delivered at a frequency between about 0.5 Hz and about 2.5 Hz.

19. A device for generating electrical pulses for inducing locomotion in an animal, comprising:

control means for controlling the generation of electrical signals having a pulse width between about 0.2 msec and about 2 msec and delivered at a frequency between about 0.5 Hz and about 10 Hz for inducing locomotion by direct spinal cord stimulation;

transmitter means connected to said control means for transmitting the electrical signals;

receiver means for placement under the skin of the animal for receiving the electrical signals and converting the signals into electrical pulses; and electrode means shaped and dimensioned so as to permit subdural or epidural implantation and connected to said receiver means, for transmitting the electrical pulses to the spinal cord, when in use, at a locus at which such stimulation induces locomotor activity.

20. The device according to claim 19, wherein said electrode means comprises at least one electrode for placement on the spinal cord and a reference electrode for placement on the vertebra.

21. The device according to claim 20, wherein said electrode means comprises at least one pair of electrodes for placement longitudinally on the spinal cord.

22. A device in accordance with claim 19, wherein said control means is for controlling the generation of electrical signals having a pulse width between about 0.2 msec and about 2 msec and delivered at a frequency between about 0.5 Hz and about 2.5 Hz.

23. A method of treating a patient with paraplegia or other disorders which impair locomotion to prosthetically induce walking comprising electrically stimulating the spinal cord of the patient using pulses having a duration of between 0.2 msec to 2 msec and a frequency between 0.5 Hz and 20 Hz wherein said stimulation is at a locus on the spinal cord at which such stimulation induces locomotor activity.

24. A method of treating a patient with paraplegia or other disorders which impair locomotion where the spinal cord has been completely or partially disconnected from the brainstem, to prosthetically induce walking comprising electrically stimulating the spinal cord of the patient using pulses having a duration of between 0.2 msec to 2 msec and a frequency between 0.5 Hz and 20 Hz wherein said stimulation is at a locus on the spinal cord at which such stimulation induces locomotor activity.

25. A device for generating electrical pulses for inducing locomotion, comprising:

control means capable of generating electrical signals having pulse widths of about 0.2 msec through about 2 msec and frequencies of about 0.5 Hz through about 20 Hz; and electrode means shaped and dimensioned so as to permit subdural or epidural implantation and connected to said control means, for receiving the signals generated by said control means and applying the signals to the spinal cord when in use.

26. A device for generating electrical pulses for inducing locomotion in an animal, comprising:

control means capable of generating electrical signals having pulse widths of about 0.2 msec through about 2 msec and frequencies of about 0.5 Hz through about 20 Hz;

transmitter means connected to said control means for transmitting the electrical signals;

receiver means for placement under the skin of the animal for receiving the electrical signals and converting the signals into electrical pulses; and electrode means shaped and dimensioned so as to permit subdural or epidural implantation and connected to said receiver means, for transmitting the electrical pulses produced by said receiver means to the spinal cord, when in use.

* * * * *

UNITED STATES PATENT AND TRADEMARK OFFICE
CERTIFICATE OF CORRECTION

PATENT NO. : 5,002,053
DATED : March 26, 1991
INVENTOR(S) : Edgar Garcia-Rill; Robert D. Skinner; Yuji Atsuta It is certified that error appears in the above-identified patent and that said Letters Patent is hereby corrected as shown below:

Column 1, line 5, after the title of the invention and prior to "Background of the Invention", insert the following:

-- This invention was made with government support under Grant No. NS20246 awarded by the National Institutes of Health. The government has certain rights in the invention. --

Signed and Sealed this

Ninth Day of November, 1993

Attest:

BRUCE LEHMAN

Attesting Officer

Commissioner of Patents and Trademarks